US009752731B2

(12) United States Patent
Goodsell

(10) Patent No.: US 9,752,731 B2
(45) Date of Patent: Sep. 5, 2017

(54) SYSTEMS AND METHODS FOR CONSERVING WATER AND OTHER RESOURCES FOR USE WITH COMMERCIAL WASHING MACHINES

(71) Applicant: Kevin C. Goodsell, Roy, UT (US)

(72) Inventor: Kevin C. Goodsell, Roy, UT (US)

(*) Notice: Subject to any disclaimer, the term of this patent is extended or adjusted under 35 U.S.C. 154(b) by 0 days.

(21) Appl. No.: 14/814,327

(22) Filed: Jul. 30, 2015

(65) Prior Publication Data

US 2016/0033086 A1 Feb. 4, 2016

Related U.S. Application Data

(60) Provisional application No. 62/032,337, filed on Aug. 1, 2014.

(51) Int. Cl.
| | | |
|---|---|---|
| *F17D 5/02* | (2006.01) | |
| *D06F 39/08* | (2006.01) | |
| *F17D 3/01* | (2006.01) | |
| *G01N 33/18* | (2006.01) | |

(52) U.S. Cl.
CPC .............. *F17D 5/02* (2013.01); *D06F 39/083* (2013.01); *F17D 3/01* (2013.01); *G01N 33/18* (2013.01)

(58) Field of Classification Search
CPC .......... F17D 5/02; D06F 39/087; G01D 11/30
USPC ...... 68/208; 222/159; 137/559, 15.01–15.26; 73/866.5
See application file for complete search history.

(56) References Cited

U.S. PATENT DOCUMENTS

| | | | | |
|---|---|---|---|---|
| 2,952,271 | A * | 9/1960 | Dick ...................... | D06F 39/08 137/360 |
| 3,707,856 | A * | 1/1973 | Niewyk .................. | D06F 33/02 68/12.03 |
| 4,485,668 | A * | 12/1984 | Hudson ................. | G01M 3/246 73/40.5 A |

(Continued)

FOREIGN PATENT DOCUMENTS

| | | |
|---|---|---|
| CN | 203203204 | 9/2013 |
| DE | 202007008555 | 10/2008 |

OTHER PUBLICATIONS

Web page http://web.archive.org/web/20131209044347/http:/www.endetec.com/en/applications/3/ Endetec; In-line Chlorine Sensors; Mar. 24, 2013.

*Primary Examiner* — Craig Schneider
*Assistant Examiner* — Nicole Gardner
(74) *Attorney, Agent, or Firm* — Workman Nydegger

(57) ABSTRACT

Systems and related methods for conserving various resources, such as, but not limited to, water, laundry chemicals, natural gas, electricity, linen, labor, and wear on equipment (e.g., a solenoid valve of a commercial washing machine drain line). The inventor has spent the past 14 years in the industrial chemical field, allowing him to access and service commercial washing machines, and has discovered that drain issues relative to such commercial washing machines result in enormous losses to such institutions that process a large volume of laundry. Such typical institutions include, but are not limited to, hotels, hospitals, prisons, universities, colleges, laundries, and nursing homes. By replacing a portion of the opaque drain pipe section between the valve and the floor drain, operators and technicians can quickly determine if a leak is occurring, and take corrective action. An access port may also be provided to test characteristics of discharged wash water.

19 Claims, 3 Drawing Sheets

(56) References Cited

U.S. PATENT DOCUMENTS

| | | | | |
|---|---|---|---|---|
| 4,649,948 A | * | 3/1987 | Hudson | F16L 41/06 137/15.11 |
| 4,883,102 A | | 11/1989 | Gabrielyan | |
| 5,029,458 A | * | 7/1991 | Obata | D06F 25/00 68/19.2 |
| 5,038,816 A | | 8/1991 | Weltsch | |
| 5,078,862 A | | 1/1992 | Justice | |
| 5,272,892 A | * | 12/1993 | Janutka | D06F 39/087 68/12.02 |
| 5,315,847 A | | 5/1994 | Takeda | |
| 5,535,779 A | * | 7/1996 | Huang | E03C 1/041 137/551 |
| 5,881,578 A | | 3/1999 | Proppe | |
| 6,183,643 B1 | * | 2/2001 | Goodley | C02F 3/301 210/151 |
| 6,199,432 B1 | * | 3/2001 | Dunn | G01L 19/0007 73/756 |
| 6,405,593 B1 | * | 6/2002 | Palfenier | G01D 11/30 73/493 |
| 6,640,825 B2 | * | 11/2003 | McAtarian | G01M 3/04 137/312 |
| 6,705,978 B2 | | 3/2004 | Pienmaki | |
| 7,637,129 B2 | * | 12/2009 | Wang | D06F 39/08 134/102.2 |
| 2003/0143887 A1 | * | 7/2003 | Rehmann | G01D 11/30 439/358 |
| 2003/0150489 A1 | * | 8/2003 | McAtarian | G01M 3/04 137/312 |
| 2007/0075093 A1 | * | 4/2007 | Thomasmeyer | B67D 3/00 222/159 |
| 2008/0092601 A1 | * | 4/2008 | Konides | D06F 35/001 68/13 R |
| 2009/0090138 A1 | * | 4/2009 | Wang | D06F 39/08 68/19 |
| 2013/0036773 A1 | * | 2/2013 | Choi | D06F 37/40 68/140 |
| 2013/0049309 A1 | | 2/2013 | Brigham | |
| 2016/0033086 A1 | * | 2/2016 | Goodsell | F17D 5/02 137/15.17 |

* cited by examiner

SYSTEMS AND METHODS FOR CONSERVING WATER AND OTHER RESOURCES FOR USE WITH COMMERCIAL WASHING MACHINES

CROSS-REFERENCE TO RELATED APPLICATION

The present application claims the benefit of U.S. Provisional Patent Application Ser. No. 62/032,337, filed Aug. 1, 2014, entitled "SYSTEMS AND METHODS FOR CONSERVING WATER AND OTHER RESOURCES FOR USE WITH COMMERCIAL WASHING MACHINES," the disclosure of which is herein incorporated by reference in its entirety.

BACKGROUND OF THE INVENTION

1. The Field of the Invention

The present invention is in the field of commercial washing machines, and more particularly to methods for reducing waste of valuable resources, such as water, laundry chemicals (e.g., detergent, bleach, softener, etc.), fuels or other energy used to heat water, linens, etc.

2. The Relevant Technology

Commercial washing machines are routinely employed in various institutions that generate large volumes of linen (e.g., towels, bedding, clothing, etc.) to be laundered. Such commercial washing machines are of a size that is significantly larger (e.g., 60 lb or more capacity) than those employed in residential environments, and are configured differently so that they drain from the bottom of the machine. In contrast, residential washing machine models may drain from anywhere along the back of the machine, but include a siphon break that forces the water in the drain line to run up the wall above the top water level associated with the washing machine, before draining into the residential sewer line. The siphon break prevents water from being inadvertently siphoned, or pulled into the sewer line, so that it only drains from the washer when desired (e.g., pumped therefrom).

In addition, such commercial washing machines typically operate on a more sophisticated wash cycle, by which a portion of the wash water is added during sub cycles of the overall wash cycle. The chemicals for the overall wash cycle are also added sequentially (and automatically), rather than all at once. For example, such a washer may add a portion of the wash water (e.g., about 13 gallons for a 60 lb capacity washer) for a first sub cycle or portion of the overall wash cycle, the water may be at least partially drained, and new wash water added for a subsequent portion of the wash cycle, etc. Such washers may include 2, 3, or more such sub cycles in the overall wash cycle. In addition, the chemicals (e.g., detergent, bleach, softener, etc.) may typically be added automatically and sequentially, during the respective sub cycle portions of the overall wash cycle, as opposed to addition of all or most all chemicals at once (e.g., manually), as is the case in residential size washers. Such commercial washers are also typically programmable, so that the operator or technician may customize the various parameters associated with the various sub cycles of the overall wash cycle (e.g., cycle time, water added, chemicals added and how much, etc.).

Commercial washing machines typically include a solenoid valve within the drain line of the washing machine, which operates to selectively open and close a valve door in the drain line, allowing the wash water to be discharged, as needed.

BRIEF SUMMARY

The present invention relates to systems and methods for conserving resources associated with commercial laundry washing machines. An exemplary system may include a commercial laundry washing machine including a valve within a drain pipe section through which wash water from the washing machine is discharged into a waste water treatment or disposal system. The system may further include a portion of the drain pipe section exterior to the washing machine and upstream from where the drain pipe empties into a floor drain, wall drain, or other drain location of the waste water treatment or disposal system that is inaccessible as a practical matter, the portion of the drain pipe section exterior to the washing machine being of a transparent material so as to allow an operator or technician to visually ascertain if water is draining through the transparent portion of the drain pipe section even though the valve (e.g., a solenoid valve) is attempting to close. The transparent portion of the drain pipe section may further comprise an access port through a top surface of the transparent portion of the drain pipe section so as to be out of a flow path of wash water in the transparent portion of the drain pipe section to allow a technician to insert a test strip through the access port into the wash water discharged from the washing machine to test pH, bleach concentration, or other chemical characteristics of the discharged wash water.

An exemplary method of conserving resources may include providing a transparent portion to a drain pipe of a commercial washing machine, which transparent portion is exterior to the washing machine, downstream from a valve of the drain pipe associated with the washing machine, and upstream from where the drain pipe empties into a drain that provides access to a waste water treatment or disposal system, which allows an operator or technician to visually ascertain if wash water is draining through the transparent drain pipe portion even though the valve of the drain pipe associated with the washing machine is attempting to close. The method may further include periodically (e.g., regularly, such as every day) checking the transparent drain pipe portion to determine if wash water is draining through the transparent drain pipe portion even though the valve is attempting to close. The method may further include repairing or replacing the valve when wash water is determined to be draining through the transparent drain pipe portion even though the valve is attempting to close.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1:
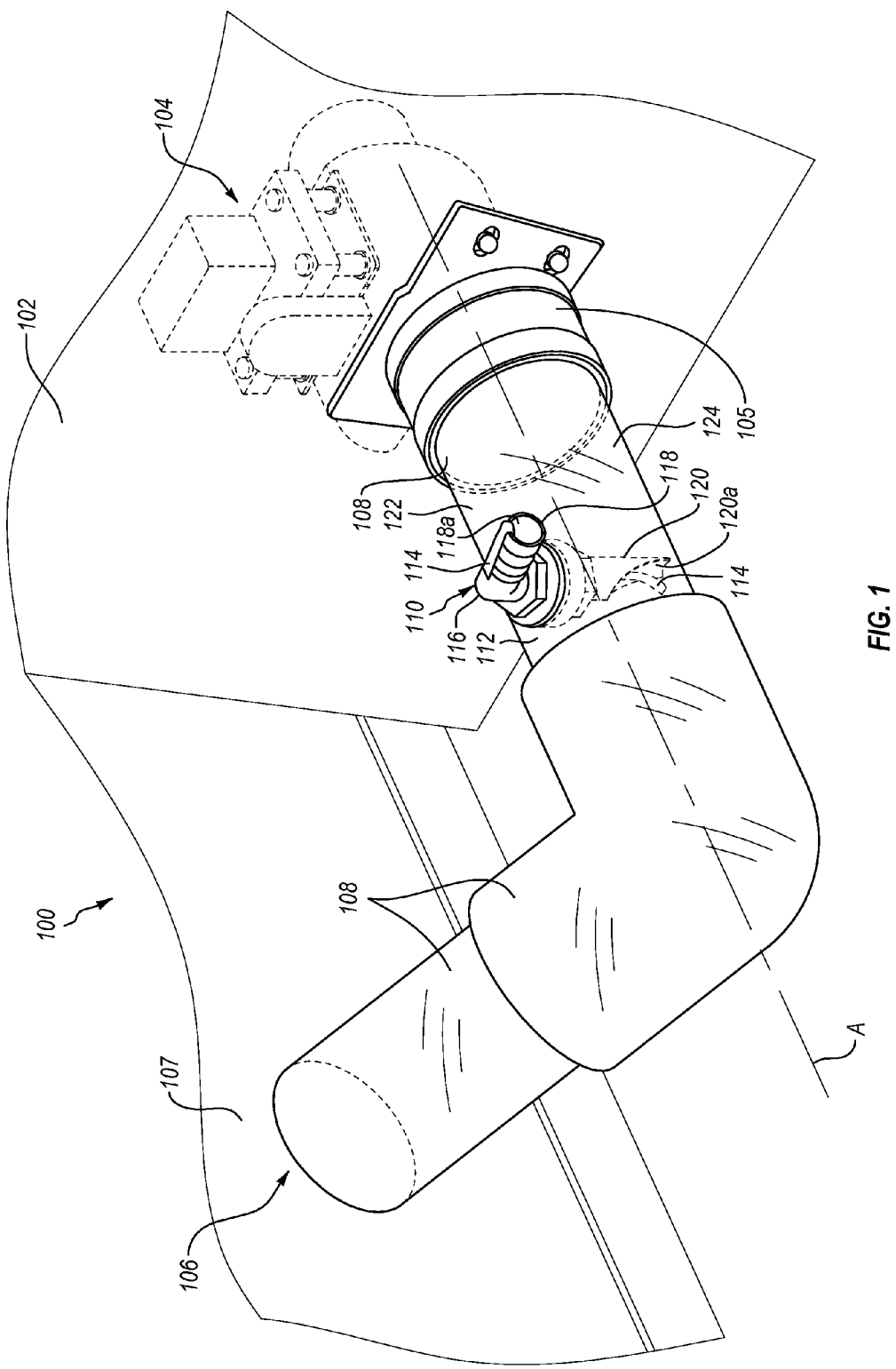
FIG. 1 shows an exemplary system according to the present invention.

The present invention relates to systems and related methods for conserving various resources, such as, but not limited to, water, laundry chemicals (e.g., detergent, bleach, softeners, etc.), natural gas, electricity, linen, labor, and wear on equipment. The inventor has spent the past 14 years in the industrial chemical field which has allowed him access to commercial washing machines, at times servicing commercial washing machines, and has discovered that drain issues relative to such commercial washing machines result in enormous losses to such institutions that process a large volume of laundry. Such typical institutions include, but are not limited to, hospitality (e.g., hotels, motels, bed and breakfasts), hospitals, corrections (e.g., prisons, jails, youth detention centers, etc.), universities, colleges, laundries (including dry and "wet" cleaners), commercial laundries (model linens), fire stations, athletic institutions (e.g., college, professional, etc.), car washes, dairies, food processing facilities (e.g., meat plants), maritime facilities (e.g., cruise ships, coast guards, etc.), restaurants, spas, salons, long term care facilities, and nursing homes.

In the inventor's experience, perhaps two-thirds of all such institutions' commercial washing machine installations have chronic leak issues associated with the drain systems for selectively draining the wash water from the commercial washing machine. In effect, the inventor has discovered that if the drain lines of such commercial washing machines are inspected, about two-thirds of them exhibit a leak where the wash water that is supposed to be held within the washer during select portions of the wash cycle is instead slowly (or not so slowly) leaking out of the drain line of the washing machine system. Such a leak (which may often appear as a continuous trickle to full on gush out of the drain system) may appear to the labor force called upon to operate such commercial washing machines as insignificant, and a mere nuisance, although the inventor has discovered that it is actually the root of a much larger and overall costly issue.

The inventor has discovered a simple solution to the present problem, which relies on education, associated intervention, and a modification to the drain pipe section exterior to the washing machine, downstream from the valve (e.g., solenoid valve) associated with the washing machine that is supposed to close during select portions of the wash cycle so as to hold the wash water in the washing machine. The modified drain pipe section is exterior to the washing machine, downstream from the described drain valve, and upstream from where the drain pipe empties into the floor drain or similar drain, of a larger (e.g., municipal) waste water treatment or disposal system. Once the water enters such drain (e.g., the drain of the building in the room in which the washers are located), it and the piping carrying it is inaccessible as a practical matter.

For example, a system according to the present invention includes a commercial laundry washing machine that includes a valve (e.g., a solenoid valve) within a drain pipe section through which wash water from the washing machine is discharged into a waste water treatment or disposal system (e.g., a municipal water treatment system). In another embodiment, the system itself may not necessarily include the washing machine, but is of course for use with the washing machine (e.g., in a retrofit). In existing installations, there is a drain pipe section exterior to the washing machine (e.g., exiting behind and at the bottom of the washing machine), upstream from where the drain pipe empties into the floor drain or similar drain. This section, often only 3-4 feet (e.g., rarely longer than 15 feet) in length simply serves to carry the dirty wash water out of the washing machine, and into the waste water treatment or disposal system (e.g., the sewer) through the building drain. This drain pipe section in existing installations is formed of an opaque (e.g., black or white) pipe material (e.g., opaque, black or white 3 inch PVC pipe). Because the drain pipe is opaque, the operator cannot readily see if any leak is present.

The present invention employs a transparent drain pipe section for at least a portion (e.g., typically all) of this drain pipe section that is exterior to the washing machine, downstream from the valve, and upstream from where the drain pipe empties into the drain serving as the entrance into the larger waste water treatment or disposal system. Employing a transparent pipe portion is a simple, but elegant solution that advantageously allows a technician or operator to readily visually ascertain if water is draining through the transparent portion of the drain pipe section, even though the solenoid valve is attempting to close (i.e., the wash water is supposed to be held within the washing machine). This often occurs when fibers or degraded linens, coins, or other debris becomes trapped against the valve door, preventing its full closure, as explained herein. Unless such debris is removed, the valve will unsuccessfully try to close as usual, eventually burning out.

Absent recognition of the particular problem to be solved, one would not readily choose to include a transparent drain pipe section as described above, as such transparent piping is many times more expensive than the typically employed opaque PVC piping.

Such a transparent portion of the drain pipe may further comprise an access port through the top surface (e.g., so as to be out of a flow path of wash water in the transparent portion of the drain pipe section) of the transparent portion of the drain pipe section. This allows a technician to insert a test strip or other testing equipment through the access port, into wash water discharged from the washing machine in order to test pH, bleach concentration, or other chemical characteristics of the discharged wash water. Without such an access port, it is impossible to test the wash water, as it only travels through the opaque drain pipe, and into the drain or sewer system, so that no access is possible. Because the modified pipe section is transparent, it is easy to visually confirm that the test strip actually contacts the wash water to be tested. This allows the technician to quickly identify other problems that may be present in the overall system (e.g., a problem with the chemical dispensing system that automatically dispenses laundry chemicals into the washing machine).

A related method includes providing such a transparent portion in a drain pipe section of a commercial washing machine, which transparent portion is exterior to the washing machine and upstream from where the drain pipe empties into the floor (and downstream from the solenoid valve or other valve which selectively holds or drains the wash water). This allows the technician or operator to visually ascertain if wash water is draining through the transparent drain pipe portion, even though the valve of the drain pipe associated with the washing machine is attempting to close. For example, the motor of such a valve (e.g., solenoid valve) may continuously attempt to close, but full closure may be impeded by linen fibers or other debris wedged between the valve door attempting to close and an adjacent sidewall of the valve. Such a condition will generally cause the solenoid motor of the valve to fail prematurely (i.e., it burns out).

A technician or operator may periodically (e.g., regularly, such as every day of use) check the transparent drain pipe portion to determine if wash water is draining through the transparent drain pipe portion, even though the solenoid valve is supposed to be closed. In the event that the wash water is draining, even when the valve is supposedly closed, the solenoid valve is repaired (e.g., cleaned and debris removed) or replaced. As described above, such leaking through the supposedly closed valve is often caused by strings or fibers of linen (e.g., generated from degrading linen) discharged with the wash water becoming caught in the solenoid valve, which prevents it from fully closing. Removing such linen or other debris materials from the solenoid valve allows the valve to again operate properly, holding the wash water in the washing machine until it is intended to be discharged.

II. Exemplary Systems and Methods

The slow leaking of a commercial washing machine through its drain line has not been regarded as a sign of a much larger problem, but merely as a nuisance. The fact is that when the commercial washing machine leaks, there is collectively a large amount of water being wasted as it continually drains, so long as the washing machine is running. When multiplied over the many commercial washing machines within a given institution, and over a metropolitan area, the volume of wasted water is very large (e.g., likely thousands of cubic feet of water, tens of thousands of cubic feet of water, or more in a month).

In addition, the drain valve (e.g., a solenoid valve) will continue to try to shut, but will not be able to do so completely, due to the linen fibers, strings, or other debris trapped in the valve. Because of the valve's continuously attempting to shut, the valve wears out much faster than it would under normal operating circumstances, where it can properly and fully shut. For example, if properly cared for, a solenoid valve as used in a commercial washing machine may typically last about 2-5 years, depending on the facility. Where the solenoid valve has linen fibers, coins, or other debris trapped against the valve door that is attempting to shut, the solenoid motor will often burn out in a matter of weeks (e.g., less than about 10 weeks), as it is continuously trying to shut so long as the washer is running and a signal is sent to the solenoid to close the valve. Thus, solving this problem allows the solenoid valve to be used over its full lifetime which is significantly longer (e.g., 10 times longer or more). It also conserves the electricity that is otherwise continuously being consumed to run the solenoid motor, which is continuously trying to shut, so long as the valve door is clogged and the valve is attempting to close.

In addition, the water leaking through the commercial washing machine, the solenoid valve, and out the drain pipe is typically hot water. In addition to the water wastage described above, there is collectively an enormous energy expenditure to heat that water that is simply being continuously discharged down the drain, so long as the commercial washing machine is running with the leak. For example, where the water heater employs natural gas in heating the water fed into the commercial washing machine, there is an associated conservation of natural gas that is then not consumed to heat the water that is otherwise being discharged down the drain. Where the water heater is electric, there is an associated conservation of electricity which is not consumed in heating the otherwise discharged water.

By way of example, if the constant trickle of water is at a rate of about 1-2 liters every 5 minutes, that equates to about 0.05-0.06 gallons per minute (GPM) (for 1 liter every 5 minutes). Where the water is leaking faster, (e.g., a full on gush), the loss is far greater (e.g., by a factor of 10 or more). Such commercial machines are often run at a rate of 12 loads or more per day, per machine (e.g., about 8-10 hours per day, per machine). In an installation of 2 machines, this trickle may collectively amount to 50 to 70 gallons of wasted hot water per day, based on a 1 liter/5 minute trickle. For a single installation, this amounts to over 20,000 gallons of wasted hot water per year. When multiplied over dozens or hundreds of institutions within a municipal area, the collective waste, just in terms of water and energy wasted to heat that water (even just directly from the leak) is enormous (e.g., millions of gallons of water per month or per year). When additional water use necessitated by the leak is figured in, the numbers become even larger (e.g., double, triple, or even a factor of 10 greater). A 2 liter/5 minute trickle would exhibit numbers double those described above.

Such waste is further exacerbated because the leak causes those linens in the washing machine to not come clean, necessitating a "reclaim" load, as described herein, and as will be understood by those of skill in the art. The reclaim load requires about another 160 gallons of hot water usage for just a single load on a typical 60 lb capacity washer. This can easily be 10 times or more the amount of water directly lost due to the leak (e.g., reclaim water usage may be considered to be an indirect loss due to the leak).

In the case of a leak that is more than the trickle described above, (e.g., a full on gush out the back end of the drain line of the washing machine), the flow rate may be 0.5 GPM to about 25 GPM, or 1 GPM to 15 GPM (e.g., the machine may fill with 20-35 gallons of water in 60 to 90 seconds at the start of a load). For a leak flow rate of about 1 GPM, the water loss is about 25 times greater than the losses described above relative to a trickle. For example, in an installation of 2 machines, such a 1 GPM leak may collectively amount to 1,250 to 1,750 gallons (e.g., about 1,500 gallons) of wasted hot water per day. For just that single installation, this amounts to over 500,000 gallons of wasted hot water per year. For a 10 GPM leak, the amounts would be 10 times greater than those for a 1 GPM leak.

One way that such full on gush leaks occur is where the fill valve responsible for filling the washing machine is clogged or has gone bad. Such fill valves are routinely referred to as Parker valves within the field. One manufacturer of such valves is Alsco Industrial Products located in Lithia Springs, Ga. An example of such a valve is seen on the 4$^{th}$ page (numbered page 2) of the Pocket Hardmount Preventative Maintenance Manual, filed as part of the above referenced provisional application. Such a valve is more or less a stop or start fill valve for the washing machine. For example, the machine sends a signal to the valve saying it needs to fill the machine. The valve opens, and water flows into the machine until the appropriate limit is reached, after which the valve is supposed to close. Rather than properly closing, sometimes a small particle, piece of metal chip, or other debris that has decayed away from the pipes or is otherwise present gets stuck in the fill valve, upstream from the washer. This causes the valve to not close all the way, and the water may stay running until someone notices it.

In the inventor's experience, nearly every time such a problem has been caught, it is the hot water that has been running continuously. When this happens the water that comes through the drain line of the washing machine is not a trickle, but is much more substantial in flow. One can sometimes hear the rushing water through the drain system, although typically people do not know where it is coming from, and it gets forgotten. There is no back-up or other system that catches this problem, and unfortunately this happens quite frequently. When this happens water goes straight through the machine and down the drain which is a major loss of hot water. This occurs even when the machine is not running (e.g., the drain valve defaults to "open" when the machine is off). Even though the Parker fill valve defaults to "close" when the machine is off, if the machine is on, or the fill valve is faulty, water may continue to run, and run, and run. When the systems as described herein are installed one would quickly be able to see the rushing water coming through the clear drain pipe and know there is a problem, prompting the operator or technician to call maintenance personnel and have the problem fixed.

In addition to conservation of water, electricity, natural gas, and life of the solenoid valve, there is an enormous savings or conservation of linen and labor where the leak is quickly detected and repaired. For example, the inventor has discovered that when a commercial washing machine constantly leaks during use, it is difficult to hold the necessary volume of water within the washing machine, as wash water is constantly leaking out. This constant leak affects the concentration of detergent, bleach, and other laundry chemicals within the wash water, as well as the pH of that wash water. It makes it difficult to maintain target concentrations of such chemicals, and can lead to variations in concentration over the wash cycle. While some washers may automatically recognize that the volume of wash water is constantly and slowly decreasing, and attempt to add new water to compensate, this loss of wash water makes it difficult to carefully control chemical concentrations. For example, where wash water is preferentially discharged through the leak as compared to chemicals that may also be entrained therein, the concentration of those chemicals retained and held in the wash water held in the washing machine actually increases. This increase can lead to chemical burns or staining of the linen. It can also result in chemical burns to those using the linen once it has been laundered. For example, it is believed that many instances of bed sores in nursing homes and hospitals are due to chemical burns where residual chemicals held in the laundered linen are released when contacted by a patient's sweat, body fluids, or other moisture sources. Upon contact with water, bleaches, pH adjusters (e.g., bases such as alkali metal hydroxides) and other chemicals held in such linens can result in chemically induced bed sores, which are often chemical burns.

On the other hand, if the chemicals mixed in the wash water are preferentially discharged through the leak, the chemical concentration drops, which can cause laundering to be ineffective in stain removal. In both instances, the continued addition of added water to the washing machine to try to compensate for such a leak further complicates the difficulty of maintaining chemical concentration and pH values within tightly desired ranges. In view of this, it will be apparent to one of skill in the art that in order to effectively clean the linens (e.g., towels, bedding, etc.) within the washing machine, it is important that these variables be tightly controlled. Constant leakage of wash water out the back of the washing machine greatly interferes with the ability to properly clean the linen in the washing machine.

As a result of the difficulty in controlling laundering conditions of chemical concentration and pH, it becomes necessary to recycle a large volume of linen for an additional treatment, because of staining in the linen which has not been removed during the normal wash cycle, or stains that are actually added during the wash cycle because of contact with too high chemical concentrations. Such stains also often become set, making their removal more difficult, if not practically impossible. When running such an additional treatment (referred to as a reclaim load), the concentrations of detergent, bleach, and/or other laundry chemicals added during the wash cycle are drastically higher, in an attempt to remove the stain. Where a leak remains present, all of the problems associated with the normal wash cycle remain. Often, a significant fraction of such retreated linens are not salvageable (particularly where a leak is present), even with repeat treatments, and are discarded (e.g., "ragged"), which collectively represents an enormous cost to the institution.

In addition, such linens which are repeatedly treated are also more likely to be damaged by the laundry chemicals themselves, due to the drastically increased concentration of such chemicals in the reclaim load wash water, even if the chemical concentrations are kept within the recommended ranges. For example, the elevated bleach and detergent concentrations lead to chemical attack of the fibers of the linen, causing such linens to exhibit shorter usable lifespan, even if the stains can be removed. For example, such linens often exhibit a tendency to fray and otherwise deteriorate along the edges of towels, bedding, and other linen. It is often these strings and fibers which become separated from the linen, and clog the solenoid valve. In addition, with higher chemical concentrations, and where a leak interferes with the ability to hold the needed volume of wash water within the washing machine, there is a higher incidence of bleach and sour softener stains, where the chemicals are too high in concentration (e.g., fully or nearly undiluted) when in contact with the linen. Such contact results in tell-tale yellow and other staining of the linens, which can be difficult if not practically impossible to remove.

As a result, a typical hotel or other institution, which may have 500-600 towels, and which might normally hope to only have to replace that linen once a year, finds it necessary to replace the linen more often, such as once every few months (e.g., every 3 to 6 months), or even more often if a leak is left unchecked. For example, a typical medium to large size hotel may replace at least $1,000 of linen every month under normal attrition circumstances. Much of this attrition is due to the issues described herein. Where there is a problem more serious than a chronic small leak, which can often occur several times a year, the problem of linen loss due to problems with the commercial washing machine installation is much greater. Such occurrences lead to linen that is stained or otherwise damaged piling up in the laundry room, which is associated with much more expensive losses than the typical $1,000 a month. For example, such hotels may typically experience at least 4-5 major breakdowns with the commercial washing machine installation, each year. In the inventor's experience, likely three out of those five break downs are due to drain issues such as described herein, that the operators could not see. With the present inventive systems and methods, such problems would be caught early on, and quickly fixed, saving on repair costs, as well as the numerous resources as described herein. For example, a repair technician may charge $85 to $150 just for the trip charge, on top of a high hourly rate.

For example, the inventor has observed that if a leak is not repaired, within a week or two, the entire linen inventory of the institution looks awful, effectively making it unsuitable for use. Hotels and similar institutions strive to keep a given "par level" of linen on hand in order to have extra linen for use. Each par level refers to the facility having enough linen on hand to completely change out all linen one time. For example, a hotel may desire to have a "3" par level of linen on hand, meaning they have enough linen on hand to completely change out the linen 3 times per room. For a typical hotel, this may represent tens of thousands of dollars to $100,000 in linen inventory. A typical hotel may have about 100 to about 200 rooms. When multiplied across multiple institutions in a given metropolitan or geographic area, the cost is many millions of dollars. Expensive linen is destroyed where a leak goes undetected, and until now, the leak of the washing machine has not been recognized as the root cause of this destruction.

Thus, the mere ignoring of a leak in the commercial washing machine can quickly lead to a very expensive problem, if not quickly addressed. In addition, most within the industry (e.g., operators, supervisors, and even many technicians) do not recognize the link between the leak and the expensive waste and damage that follows. As described above, there is an enormous savings that could be achieved in water, natural gas, electricity, labor, and linen costs by simply implementing the present systems and methods.

The present invention seeks to address these issues by providing a mechanism by which the operators and technicians who work with the commercial washing machines every day can be educated as to the problem, and can be provided with a mechanism by which a leak can be identified very soon after it first appears. Once the leak is identified, it can quickly be repaired (e.g., by removing linen fibers, coins, or other debris that is blocking the door of the solenoid valve which is trying to close), so that linen is not destroyed, the solenoid valve motor does not burn out, and other resources (e.g., water, chemicals, natural gas, electricity) are not wasted. Rather, the problem is quickly identified and repaired, before significant waste or damage can occur.

As outlined above, the scale of the present problem is not minor, being limited to a small number of commercial washing machines. For example, in the inventor's experience, the volume of water used by one 60 lb commercial washing machine in a typical large hotel is about 67,000 ft$^3$ (over 500,000 gallons) per month. A significant fraction of this is attributable to the commercial washing machine installation. Where perhaps two-thirds of such commercial washing machines leak at a slow but steady trickle due to clogging of the door associated with the solenoid valve, a significant fraction of this water volume could be conserved by employing methods and systems as described herein. For example, a significant fraction of this water volume can be directly linked to leakage through the system, as it simply passes through the washing machine and leaks out the back, continuously, so long as the washing machine is running, and the valve is attempting to close. This leaking water volume is significant. For example, in many installations, the washing machines may be run at a rate of 12 loads per day, per washer. Many installations have 2 or more washers. Another fraction of this water volume, which may likely be an even higher fraction, can be directly linked to "reclaim" loads, where linen that was washed, but did not come clean, is run through the washing machine again, under different conditions, as described above.

The waste thus becomes quite large even for a single installation including 1-3 commercial capacity washing machines at 60 lbs to 80 lbs capacity per machine. The waste of water and other resources becomes enormously large (e.g., likely representing millions of gallons of water per year when accumulated over even a moderately sized metropolitan area). The loss in labor, electricity, natural gas, chemicals, and other resources easily reaches into millions of dollars per year over that same metropolitan area.

Reclaim loads include much higher levels of chemicals added to the load in an attempt to "reclaim" that linen which is otherwise lost (e.g., turned into rags). In addition to the higher chemical loading, such loads are often run according to a different wash cycle, which consumes a greater volume of water. For example, a normal load of white towels run on a 60 lb capacity UniMac or Milnor commercial washing machine may consume about 116 or 124 gallons of water, per load, respectively (i.e., in either case, about 120 gallons). A reclaim load of white towels that did not come clean in the normal load in the same commercial washing machine is run according to a wash cycle that consumes about 165 gallons, or 150 gallons of water, respectively (i.e., in either case, about 160 gallons).

In addition, the cost of chemicals (e.g., detergent, bleach, softener, etc.) in the reclaim load is significantly more (e.g., several times more) than the cost of the normal load. For example, typical chemical cost of the normal load may be about $1.43 for a 60 lb capacity commercial washing machine. Due to the addition of additional chemicals, and using more of those chemicals used in the normal load, the chemical cost when running a reclaim load may be about $6.44, which is 4 to 5 times greater than that of the normal load.

As will be apparent, if the present systems and methods allow one to not have to run so many reclaim loads, the savings in chemicals, water (e.g., hot water), labor, electricity, and other resources is significant for each reclaim load that is not needed because leaks are being detected and quickly repaired. Leaks interfere with the ability of the commercial washing machine to hold the needed volume of wash water. Even though the commercial washing machine may constantly be trying to replace leaking water, in the inventor's experience, the results speak for themselves. As described above, it is not a simple matter of water being lost. Rather, the inventor has observed that in instances where there is a leak, it adversely affects the ability of the washing machine to effectively clean the linen load. As a result, when the load has finished its cycle, it is likely to not have come clean (e.g., due to much of the chemicals that should have been held in the wash water instead leaking out the back end of the washing machine, lack of control over chemical concentrations due to the leak, etc.). As a result, much or all of the load may have to be placed aside, to be rerun in a "reclaim" load. When servicing commercial washing machine installations, the inventor has often observed bins full of linens that did not come clean, to be rerun in a reclaim load. The inventor has observed that there is a correlation between such installations having a backlog of linen to be "reclaimed" and that installation having washing machines that are leaking Photos of such installations where linens to be run in a reclaim load are stacked in bins are shown in the Appendix of the above referenced provisional application.

In environments where water is a scarce resource, such as the western United States, the problems described represent a significant waste and loss of a valuable resource. As described above, water waste is not the only waste associated with this problem and addressed or conserved by the present invention, as there is also conservation of laundry chemicals, lengthened life of linens which are collectively very expensive, conservation of natural gas and electricity, longer life in the solenoid valve, and overall lower labor costs, as fewer loads of linens are required to be retreated.

FIG. 1 illustrates an exemplary drain system 100 and upstream solenoid valve 104 where a portion 108 of the drain system exterior to the washing machine is transparent. The transparent portion 108 of the drain pipe is downstream from the solenoid valve 104, and upstream from where the drain pipe discharges into the floor drain or wall drain 107 (i.e., the access point into the larger waste water treatment or disposal system) allowing the operator to quickly and easily visually ascertain if the solenoid valve 104 is unable to fully close, causing a leak.

Figure 2:
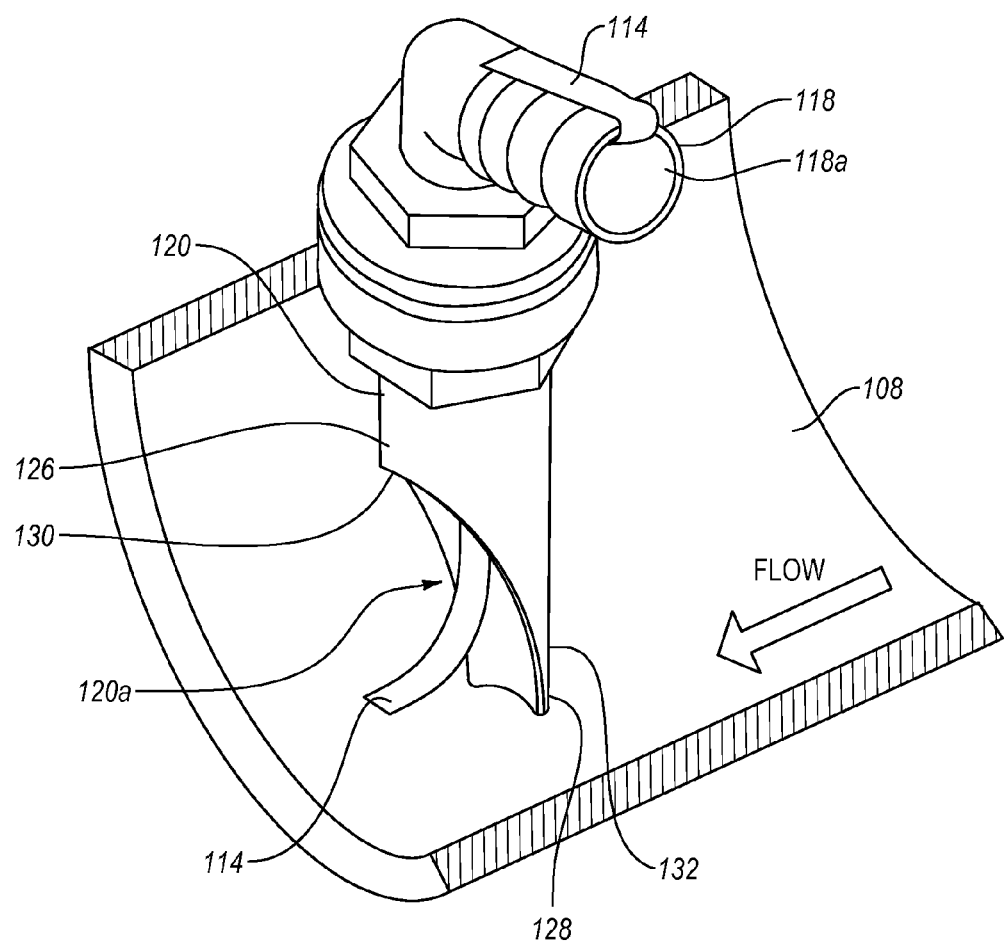
FIG. 2 is a close up view showing an exemplary access port included in a transparent drain pipe section according to the present invention.

FIG. 2 shows a close up of the access port, illustrating a preferred configuration of the outlet leg of the elbow of the access port, so as to prevent wash water in the drain pipe from catching on the outlet leg of the elbow and splashing into and through the access port, and being propelled to the exterior of the drain pipe. It will be appreciated that the drain line is thus not pressurized.

As seen in the Figures, an embodiment of the present inventive system 100 configured to conserve resources may include a commercial laundry washing machine 102 including a solenoid valve 104 within a drain pipe section 105 through which wash water from washing machine 102 is discharged into a waste water treatment or disposal system 106. A portion 108 of the drain pipe 105 exterior to the washing machine and upstream from location 106 where the drain pipe 105 empties into floor drain or wall drain 107 is advantageously transparent so as to allow a technician or operator to visually ascertain if water is draining through transparent portion 108 of drain pipe 105, even though solenoid valve 104 is attempting to close.

The transparent portion 108 of drain pipe 105 may further include an access port 110 substantially through top surface 112 of transparent portion 108 of drain pipe 105. Access port 110 so placed advantageously allows a technician to insert a test strip 114 through port 110 into wash water discharged from the washing machine 102 to test pH, bleach concentration, or other chemical characteristics of the discharged wash water. Port may be disposed through the top surface 112 as shown, or substantially (e.g., near) top surface 112. By substantially, it is meant that the location may be out of a flow path of wash water in the transparent portion of the drain pipe section. For example, it may be advantageous to ensure that the port 110 is not in the bottom of pipe portion 108. For example, if disposed somewhat off center relative to top 112, it may still be disposed above a half-way point between the bottom and top 112 (i.e., closer to top than bottom).

FIG. 2 illustrates a close up view of an exemplary access port 110. Port 110 may include an elbow 116 (e.g., about 90°) including an inlet leg 118 and an outlet leg 120. At least proximal end 118a of inlet leg 118 may be disposed exterior to drain pipe 108, and may extend substantially perpendicular and laterally (e.g., sideways) relative to a longitudinal axis A of the drain pipe section in which the port 110 is disposed. Outlet leg 120, or more particularly at least distal end 120a thereof, may be disposed interior to drain pipe 108. Outlet leg 120 may lead into a top interior portion 122 of transparent pipe portion 108, and leg 120 may be oriented so that leg 120 extends towards bottom interior portion 124, where the discharged wash water flows. Leg 120 may be substantially perpendicular and oriented downward relative to axis A of transparent drain pipe portion 108. Legs 118 and 120 may be substantially perpendicular relative to one another.

As perhaps best seen in FIG. 2, distal end 120a of leg 120 disposed within the interior of drain pipe 108 may include a sidewall (e.g., a circular sidewall) 126 which is tapered so as to be longer on upstream side 128 versus downstream side 130. In the illustrated embodiment, this taper is achieved by providing the opening in distal end 120a with a curved, scooped shape so that upstream portion 128 serves as a shield 132 to prevent or minimize wash water flowing within drain pipe section 108 from entering into access port 110. In other words, that portion of the opening in distal end 120a adjacent upstream side 128 may be vertically lower in tube section 108 (i.e., closer to the flowing discharged wash water) than that portion of the opening in distal end 120a adjacent downstream side 130. For example, where no taper is provided, or where the downstream side 130 of sidewall 126 were longer than upstream side 128, there may be a tendency for flowing wash water to hit the inside surface of sidewall 126 on side 128, and be propelled up into the lumen of hollow legs 120 and 118. Rather, the wash water first hits the exterior surface at 128, rather than its interior surface. Providing an elbow bend between legs 118 and 120, as well as providing the described taper and/or curved or scooped opening at end 120a minimizes or prevents any tendency of the wash water to be propelled up into port 110, and through the proximal entrance at end 118a.

Figure 3:
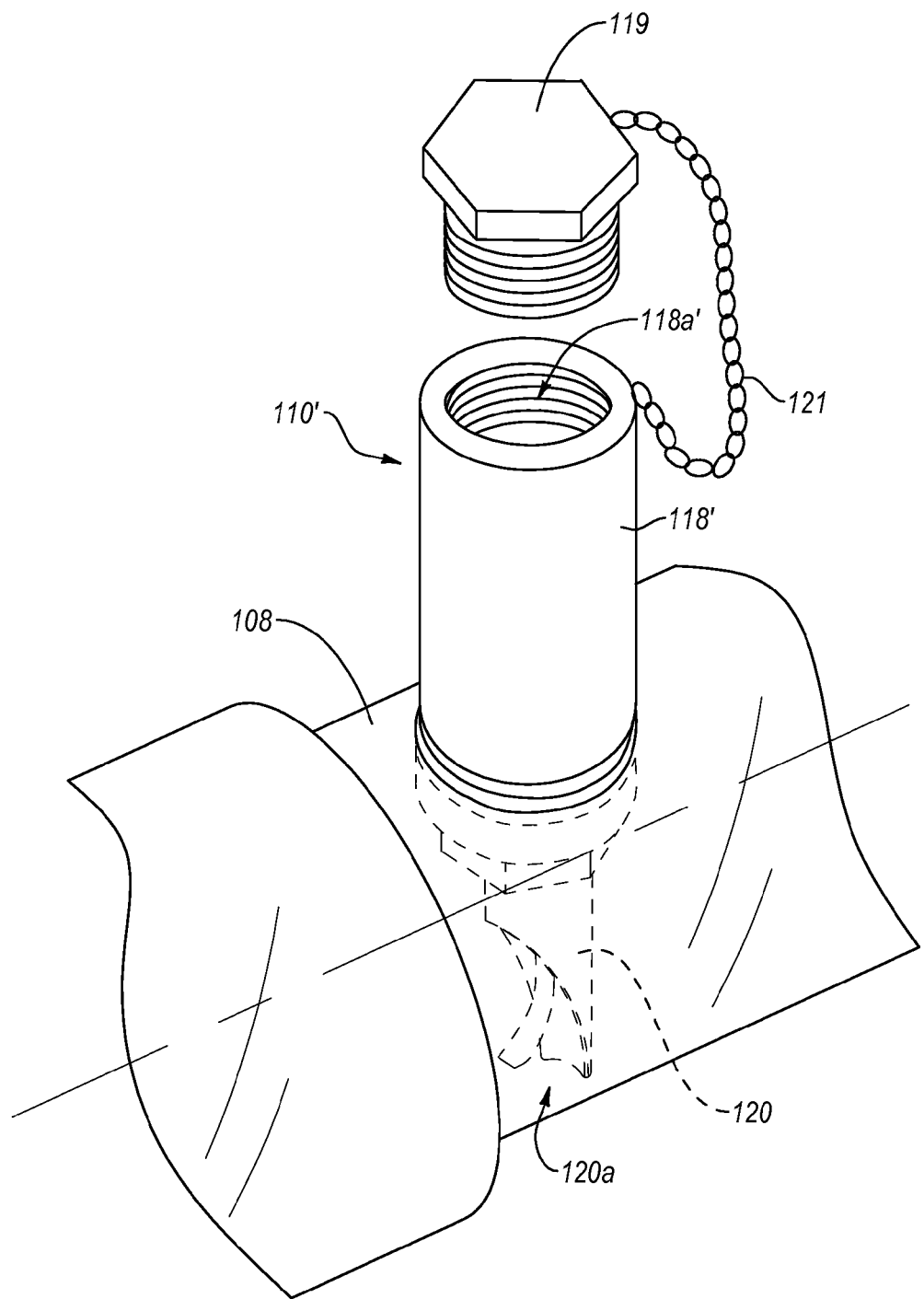
FIG. 3 is a close up view of another exemplary access port.

FIG. 3 illustrates another configuration of an access port that may be included within the present invention. Access port 110' may be similar to port 110 of FIG. 2, but is shown as including an exterior inlet leg 118' that is generally vertical, rather than including an elbow bend between legs 118 and 120. Port 110' is shown as including a cap 119 which may be coupleable over or in inlet opening 118a' (e.g., through threads or another suitable mechanism (e.g., a snap fit or friction fit cap or plug). As shown, cap 119 may include a tether 121 (e.g., a chain, rope, cord, wire, etc.) attached to both cap 119 on one end and to leg 118' or pipe 108 at the other end.

Many installations discharge into a drain in a floor or wall, as illustrated. Such a drain provides an access point to a larger waste water treatment or disposal system (e.g., a sewer system). Once entering drain at the floor or wall 107, the wash water and the piping conveying it is largely inaccessible, as a practical matter (e.g., it is encased in a wall, floor, underground, etc.). As such, it is advantageous that the transparent section 108 be disposed upstream from such drain. In some installations, a plurality of commercial washing machines (e.g., side by side) discharge into a common trough, which trough then empties into a drain (e.g., in a floor) that leads to the larger (e.g., municipal) waste water treatment or disposal system. Photographs of such a trough system are included in the Appendix of the above referenced provisional application.

An associated method of use for conserving resources may include providing a transparent portion 108 to a drain pipe 105 of a commercial washing machine 102, where the transparent portion 108 is exterior to washing machine 102, and upstream from where drain pipe 105 empties into a floor drain or wall drain 107. This advantageously allows an operator or technician to quickly visually ascertain if wash water is draining through the transparent drain pipe portion, even though valve 104 is supposed to be closed. The method further includes periodically checking transparent drain pipe portion 108 to determine if wash water is draining through the transparent portion 108, even though valve 104 is supposed to be closed. Where such leaking is occurring, the method further comprises repairing or replacing the valve 104 when it is determined that wash water is draining through transparent pipe section 108, even though valve 104 is supposed to be closed.

Such methods may be performed in an environment where the entire drain pipe 105 is initially of an opaque material (e.g., opaque PVC), where a portion 108 thereof is removed and replaced (e.g., retrofitted) with a transparent pipe section 108. As described above, the section of drain pipe between the washing machine and the drain that accesses the waste water treatment or disposal system (e.g., sewer) may often be 3 to 4 feet, or as much as 15 feet in length. All or just a portion of such pipe section may be retrofitted or provided so as to be transparent. All that is required is a sufficiently long transparent section (e.g., a foot or two, at least), that allows an operator or technician to visually determine whether a leak is occurring or not. Of course, it may be easier and preferable to simply replace the entire opaque pipe section, as it is typically not particularly long, and avoids any complications associated with splicing in a new pipe section.

Once such retrofitting occurs, or in a new installation where a portion 108 of the drain pipe is specifically installed so as to be transparent, the operator(s) of the commercial washing machine may be instructed to periodically and regularly (e.g., each day) check transparent pipe section 108 to determine if there is a leak. In the event of a leak, a service technician is contacted so that valve 104 can be repaired (e.g., cleaned to remove fibrous linen strings, coins, or other debris), or replaced if the valve is broken (e.g., the motor has burned out), or repair or replacement of a faulty fill valve. In an embodiment, a leaking washing machine may be taken off line and not used until the leaking valve is repaired or replaced, particularly if there are sufficient washing machines that the leaking machine does not need to be used. Repair may preferably occur within 1-3 days.

Without recognition of the problems that result from not recognizing and fixing such leaks, there is no reason one would include a transparent portion in the pipe section, as transparent PVC is much more expensive than the ordinarily used opaque PVC pipe materials. For example, transparent 3 inch inside diameter PVC pipe currently costs about 3 to 4 times the cost of otherwise similar parts formed from the standard opaque 3 inch diameter pipes.

Such methods advantageously enable problems caused by a leak to be quickly addressed, rather than allowing the washing machine to continue to leak. Although to many such a leak may appear insignificant, as described herein, such a leak is the root cause of numerous problems that quickly become expensive in both cost and resource consumption if left unfixed.

In addition, the presence of access port 110 in drain pipe 105 (particularly in transparent section 108—allowing the technician to visually see that the test strip is contacted with the discharged wash water) allows the technician to test or measure pH, bleach concentration or other chemical characteristics of the discharged wash water (e.g., either leaking wash water or water that is intentionally being discharged). For example, inserting a test strip through access port 110 allows the technician to know if a squeeze tube on a chemical dispenser (e.g., for detergent, bleach, softener, etc.) has gone bad, which is often the case where the pH or bleach concentration is either too high or too low. Photographs in the Appendix of the above referenced provisional application show a bank of such chemical dispensers configured to draw chemical from 5 gallon containers of the appropriate chemical (e.g., detergent, bleach, softener, etc.) for metered delivery to the washing machine. As described above, in order to preserve the longest life possible for the linen being laundered, it is important that the bleach concentration, detergent concentration, and pH be carefully maintained within a desired narrow range. Leaking of the wash water through a solenoid valve in need of repair or replacement makes it very difficult to maintain the desired levels. Similarly, a squeeze tube or other chemical dispenser mechanism in need of replacement or repair also makes it difficult to maintain the desired levels. As described above, where a system is out of whack due to such issues, within a week or two, linen being laundered looks awful, and will need to be replaced, which is an enormous expense.

The Appendix attached to the provisional application includes materials relative to cost of linen, rate at which linens are stained, costs to attempt to reclaim stained linens (e.g., about 90% of stained linen can typically be reclaimed in a subsequent washing—at higher chemical concentrations than a normal washing). Such reclaim loads more than double the water and labor consumed as compared to what would be needed if the reclaim load is made necessary in the first place because of a leak in the drain pipe system of the commercial washing machine. Of course, for such reclaim loads, the cost of chemicals is dramatically higher than for a normal load, because higher chemical concentrations are used, and additional chemicals not used in a normal washing are also often added.

Table 1 below provides an example of chemical costs and water usage for a normal load of white towels on two (UniMac and Milnor) exemplary 60 lb capacity commercial washing machines.

TABLE 1

Breakdown cost on chemicals, water and linen
Chemical cost per load based on a white towel formula on a 60 Lb industrial washer

| Laundry Product | Size | $ per pail | $ per gal | $ Per Once | Oz per load | $ per load |
|---|---|---|---|---|---|---|
| Detergent | 5 Gallon Pail | $124.00 | $24.80 | $0.19 | 3.5 | $0.68 |
| Bleach | 5 Gallon Pail | $ 37.75 | $ 7.55 | $0.06 | 3.5 | $0.21 |
| Neutralizer | 5 Gallon Pail | $101.25 | $20.25 | $0.16 | 2 | $0.32 |
| Softener | 5 Gallon Pail | $ 71.75 | $14.35 | $0.11 | 2 | $0.22 |
| Total cost per load | | | | | | $1.43 |

TABLE 1-continued

| Time | Cycle | Water level | Gallons used | Temp |
|---|---|---|---|---|
| Breakdown on water for a white towels formula on a 60 lb industrial Uni Mac washer | | | | |
| Two minutes | Per wash | High | 24.4 | Warm |
| Seven minutes | Wash | Low | 14.4 | Hot |
| Seven minutes | Wash | Low | 14.4 | Hot |
| Two minutes | Wash | High | 24.4 | Hot |
| Two minutes | Wash | High | 24.4 | Medium |
| Four minutes | Wash | Low | 14.4 | Medium |
| Seven minutes | Final Extract | | | |
| Wash Time | 27 minutes | Total gallon | 116.4 | |
| Total time with fills | 38 minutes | | | |
| Breakdown on water for a white towels formula on a 60 lb industrial Milnor washer | | | | |
| Two minutes | Per wash | High | 35 | Warm |
| Seven minutes | Wash | Low | 11 | Hot |
| Seven minutes | Wash | Low | 11 | Hot |
| Intermediate Extract 2 min | | | | |
| Two minutes | Wash | High | 28 | Hot |
| Two minutes | Wash | High | 13 | Medium |
| Intermediate Extract 2 min | | | | |
| Four minutes | Wash | Low | 26 | Medium |
| Seven minutes | Finale Extract | | | |
| Wash Time | 35 minutes | Total gallon | 124 | |
| Total time with fills | 48 minutes | | | |

On this Salt Lake City Hilton Property they used 67,800 cubic feet of water on a 30 day billing cycle that's $746.66 This property has two 60 Lb washers washing on average 12 loads a day that's 1396.8 gallons a day going down the drain if the drain system is clogged or the drain solenoid is not working properly. There are 7.480 gallons of water in a cubic foot. Below is a conversion chart

| | How Many CF | Cost per | Total on water |
|---|---|---|---|
| Enter how many cubic feet used | 67,800 | 0.011012684 | $746.66 |
| How many gallons used and cost per gallon | 507,144 | 0.001472284 | $746.66 |

Cost of the linen being washed on a 60 Lb industrial washer

| Linen | Cost per | How many | Total |
|---|---|---|---|
| Bath Mats | $ 2.44 | 100 | $ 244.00 |
| Bath Towels | $ 4.11 | 150 | $ 616.50 |
| Hand Towels | $ 1.04 | 240 | $ 249.60 |
| Washcloths | $ 0.64 | 240 | $ 153.60 |
| Pool Towels | $ 4.63 | 150 | $ 694.50 |
| King Flat | $ 8.42 | 24 | $ 202.08 |
| King Fitted | $ 8.22 | 24 | $ 197.28 |
| King Mattress Pad | $ 13.63 | 24 | $ 327.12 |
| King Bedskirt | $ 30.47 | 15 | $ 457.05 |
| Queen Flat | $ 7.10 | 30 | $ 213.00 |
| Queen Fitted | $ 7.27 | 30 | $ 218.10 |
| Queen Mattress Pad | $ 10.98 | 30 | $ 329.40 |
| Queen Bedskirt | $ 27.80 | 18 | $ 500.40 |
| Full Flat | $ 6.85 | 30 | $ 205.50 |
| Full Fitted | $ 6.98 | 30 | $ 209.40 |
| Full Mattress Pad | $ 9.89 | 30 | $ 296.70 |
| Pillow Cases | $ 1.52 | 216 | $ 328.32 |
| Queen Duvet Covers | $ 24.35 | 5 | $ 121.75 |
| King Duvet Covers | $ 25.67 | 5 | $ 128.35 |
| Sage Blanket | $ 32.61 | 22 | $ 717.42 |
| King Coverlett | $117.00 | 15 | $1,755.00 |
| Queen Coverlett | $112.00 | 15 | $1,680.00 |
| King Duvet | $ 35.00 | 22 | $ 770.00 |
| Queen Duvet | $ 33.00 | 7 | $ 231.00 |
| Pillow Protectors | $ 1.28 | 216 | $ 276.48 |
| Kitchen Towels | $ 0.00 | 260 | $ 0.00 |
| Crib Sheets | $ 5.70 | 45 | $ 256.50 |

Table 2 below provides an example of chemical costs and water usage for a reclaim load of white towels on two (UniMac and Milnor) exemplary 60 lb capacity commercial washing machines.

TABLE 2

Breakdown cost on chemicals, water and linen
Chemical cost per load based on a Reclaim formula on a 60 Lb industrial washer
A Reclaim load it is a last ditch effort to save the linen before being forced to rag it.
A reclaim load requires more chemicals.
Before starting the Reclaim load the user pours in a packet of Power Wash and
two cups of S-99. Typically, 90% of stained linen can be saved.

| Laundry Product | Size | $ per pail | $ per gal | $ Per Once | Oz per load | $ per load |
| --- | --- | --- | --- | --- | --- | --- |
| Power Wash | 15 × 1 24 oz | $ 65.50 | $ 4.37 | 1 packet | 1 packet | $4.37 |
| S-99 use 2 cups | 50 Lb box | $ 77.04 | $ 1.54 | $0.10 | 2 | $0.19 |
| Detergent | 5 Gallon Pail | $124.00 | $24.80 | $0.19 | 5 | $0.97 |
| Bleach | 5 Gallon Pail | $ 37.75 | $ 7.55 | $0.06 | 5 | $0.29 |
| Neutralizer | 5 Gallon Pail | $101.25 | $20.25 | $0.16 | 2.5 | $0.40 |
| Softener | 5 Gallon Pail | $ 71.75 | $14.35 | $0.11 | 2 | $0.22 |
| Total cost per load and customer saves 90% of stained linen | | | | | | $6.44 |

| Time | Cycle | Water level | Gallons used | Temp |
| --- | --- | --- | --- | --- |
| Breakdown for a Reclaim formula on a 60 lb Uni Mac industrial washer | | | | |
| 30 min Reclaim | Wash | High | 24.4 | Hot |
| Two minutes | Per wash | High | 24.4 | Hot |
| Two minutes | Per wash | High | 24.4 | Hot |
| Seven minutes | Wash | Low | 14.4 | Hot |
| Seven minutes | Wash | Low | 14.4 | Hot |
| Two minutes | Wash | High | 24.4 | Hot |
| Two minutes | Wash | High | 24.4 | Medium |
| Four minutes | Wash | Low | 14.4 | Medium |
| Seven minutes | Final Extract | | | |
| Total time | 72 minutes | Total gallon | 165.2 | |
| Breakdown for a Reclaim formula on a 60 lb Milnor industrial washer | | | | |
| 30 min Reclaim | Wash | Medium | 35 | Hot |
| Two minutes | Per wash | High | 13 | Hot |
| Two minutes | Per wash | High | 13 | Hot |
| Seven minutes | Wash | Low | 11 | Hot |
| Seven minutes | Wash | Low | 11 | Hot |
| Intermediate Extract 2 min | | | | |
| Two minutes | Wash | High | 28 | Hot |
| Two minutes | Wash | High | 13 | Medium |
| Intermediate Extract 2 min | | | | |
| Four minutes | Wash | Low | 26 | Medium |
| Seven minutes | Finale Extract | | | |
| Total time | 72 minutes | Total gallon | 150 | |

Powerwash and S-99 are simply examples of products from one manufacturer that can typically be added to a reclaim load, in a last ditch effort to save the linen. Such products are generally added to provide increased concentrations of detergents, destaining agents, and to drastically increase the pH (e.g., sodium hydroxide or other caustics). For example, the pH in a reclaim load may be as high as 13 or 14.

As shown in Tables 1 and 2, for such a 60 lb load of white towels, the loss in linen cost is over $600 if the stained towels cannot be reclaimed. Although 90% of the material in the reclaim load can typically be saved if the system is working properly, where there are leaks or other problems as described herein, the percentage saved can be significantly lower. Even if they can be reclaimed, it costs twice or more the labor costs (to have the operators run the load through again, as a reclaim load), and there are chemical costs of over $6 (4 to 5 times that of a normal load) for the single reclaim load, and the water usage is an additional 150-165 gallons. This does not include the costs associated with electricity to run the reclaim load, natural gas (or electricity) to heat the additional 150-165 gallons of water used in the reclaim load, or the volume of water wasted as a direct result of the leaking solenoid valve.

The appendix attached to the provisional application includes similar data for a larger 80 lb capacity washing machine. As will be apparent, for such larger washing machines, the losses are even greater.

When such wasted resources and costs are multiplied over a large number of commercial washing machines, over a large number of installations (e.g., hotels, prisons, universities, assisted living centers, nursing homes, cruise ships, hospitals, cleaners, etc.) the waste and cost becomes very large. The savings and conservation achieved by each installation, and within a metropolitan area as a whole (particularly a relatively arid region such as areas of the western United States where water is scarce) becomes significant and very large.

Thus, although the systems and methods described herein are simple and relatively easy to implement, the advantages associated with their use and implementation would make a significant difference in those communities where implemented.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system configured to conserve resources, for use with a commercial laundry washing machine including a valve within a drain pipe section through which wash water from the washing machine is discharged into a waste water treatment or disposal system, the commercial laundry washing machine draining from a bottom of the washing machine, without any siphon break between the commercial laundry washing machine and where the wash water is discharged into the waste water treatment or disposal system, the system comprising:
   a portion of the drain pipe section exterior to the washing machine, upstream from where the drain pipe empties into a floor drain, or wall drain, at or below the bottom of the commercial laundry washing machine, the portion of the drain pipe section exterior to the washing machine and at or below the bottom of the washing machine being of a transparent material so as to allow an operator or technician to visually ascertain if water is draining through the transparent portion of the drain pipe section even though the valve is attempting to close.

2. A system as recited in claim 1, wherein the valve is a solenoid valve.

3. A system as recited in claim 1, wherein the transparent portion of the drain pipe section is downstream from the valve and upstream from the floor drain or wall drain.

4. A system as recited in claim 1, wherein the drain pipe section is unpressurized, the transparent portion of the drain pipe section further comprises an access port through a top surface of the transparent portion of the drain pipe section so as to be out of a flow path of wash water in the transparent portion of the drain pipe section to allow a technician to insert a test strip through the access port into the wash water discharged from the washing machine to test pH, bleach concentration, or other chemical characteristics of the discharged wash water.

5. A system as recited in claim 4, wherein the access port includes an elbow including an inlet leg, at least the proximal end of the inlet leg being disposed exterior to the drain pipe section, the inlet leg being disposed adjacent an outlet leg of the elbow, the outlet leg leading into a top interior portion of the transparent portion of the drain pipe section, oriented so that the outlet leg extends towards a bottom interior portion of the transparent portion of the drain pipe section.

6. A system as recited in claim 5, wherein the inlet leg is oriented so as to be substantially perpendicular and laterally sideways relative to a longitudinal axis of the portion of the drain pipe section in which the access port is disposed, the outlet leg being oriented so as to be substantially perpendicular and downward relative to the longitudinal axis of the portion of the drain pipe section in which the access port is disposed.

7. A system as recited in claim 6, wherein the outlet leg is substantially perpendicular relative to the inlet leg.

8. A system as recited in claim 6, wherein the distal end of the outlet leg disposed within the interior of the drain pipe section includes a sidewall which is tapered so as to be longer on an upstream side versus the downstream side.

9. A system as recited in claim 8, wherein an opening in the distal end of the outlet leg includes a curved scooped shape so that the upstream portion of the sidewall serves as a shield to minimize or prevent wash water flowing within the drain pipe section from entering into the access port.

10. A system as recited in claim 1, wherein the system further comprises the commercial laundry washing machine including a valve within a drain pipe section through which wash water from the washing machine is discharged into a waste water treatment or disposal system.

11. A system configured to conserve resources, for use with a commercial laundry washing machine including a solenoid valve within an unpressurized drain pipe section through which wash water from the washing machine is discharged into a waste water treatment or disposal system, the commercial laundry washing machine draining from a bottom of the washing machine, without any siphon break between the commercial laundry washing machine and where the wash water is discharged into the waste water treatment or disposal system, the system comprising:
   a portion of the unpressurized drain pipe section exterior to the washing machine, downstream from the solenoid valve, at or below the bottom of the commercial laundry washing machine, and upstream from where the drain pipe empties into a floor drain or wall drain that provides access to the waste water treatment or disposal system being of a transparent material so as to allow an operator or technician to visually ascertain if water is draining through the transparent portion of the drain pipe section even though the solenoid valve is attempting to close;
   the transparent portion of the drain pipe section further comprising an access port through a top surface of the transparent portion of the drain pipe section to allow a technician to insert a test strip through the access port into wash water discharged from the washing machine to test pH, bleach concentration, or other chemical characteristics of the discharged wash water.

12. A system as recited in claim 11, wherein the system further comprises the commercial laundry washing machine including a solenoid valve within a drain pipe section through which wash water from the washing machine is discharged into a waste water treatment or disposal system.

13. A method of conserving resources, the method comprising:
   providing a rigid transparent pipe portion to a rigid drain pipe of a commercial washing machine, which transparent pipe portion is exterior to the washing machine, downstream from a valve of the drain pipe associated with the washing machine, upstream from where the drain pipe empties into a drain that provides access to a waste water treatment or disposal system, the commercial washing machine draining from a bottom of the washing machine, without any siphon break between the commercial washing machine and where the wash water is discharged into the waste water treatment or disposal system, the transparent pipe portion of the drain pipe being at or below the bottom of the commercial laundry washing machine, which transparent pipe portion allows an operator or technician to visually ascertain if wash water is draining through the transparent drain pipe portion even though the valve of the drain pipe associated with the washing machine is attempting to close; and periodically checking or instructing a user to check the transparent drain pipe portion to determine if wash water is draining through the transparent drain pipe portion even though the valve is attempting to close; and repairing or replacing, or instructing a user to repair or replace the valve when wash water is determined to be draining through the transparent drain pipe portion even though the valve is attempting to close.

14. A method as recited in claim 13, wherein the valve is a solenoid valve.

15. A method as recited in claim 13, wherein providing a portion of the drain line comprises retrofitting the portion of the drain line of the commercial washing machine by replacing a portion of an opaque drain pipe section exterior to the washing machine and upstream from where the drain line empties into the waste water treatment or disposal system with a transparent drain pipe section, which allows an operator or technician to visually ascertain if water is draining through the transparent drain pipe portion even though a valve of the drain line associated with the washing machine is attempting to close.

16. A method as recited in claim 13, wherein the drain that provides access to a waste water treatment or disposal system is in a floor or wall.

17. A method as recited in claim 13, wherein the transparent drain pipe portion is checked each day of use of the commercial washing machine to determine if wash water is draining through the transparent drain pipe portion even though the valve is attempting to close.

18. A method as recited in claim 13, the method further comprising inserting or instructing a technician to insert a test strip through an access port provided in the transparent drain pipe portion, into wash water discharged from the washing machine to test pH, bleach concentration, or other chemical characteristics of the discharged wash water.

19. A method as recited in claim 13, the method further being for monitoring and maintaining the commercial washing machine, wherein:

the transparent portion of the drain pipe is rigid;

the transparent pipe portion drains from the bottom of the commercial washing machine into a floor drain; and wherein repairing or replacing, or instructing a user to repair or replace the valve comprises checking a valve door of the valve for fibers, degraded linens, or coins trapped against the valve door, preventing full closure of the valve door, the method further comprising removing any fibers, degraded linens, or coins that may be preventing closure of the valve door.

* * * * *